(12) United States Patent
Bauer et al.

(10) Patent No.: US 7,214,935 B2
(45) Date of Patent: May 8, 2007

(54) TRANSMISSION ELECTRON MICROSCOPY SAMPLE PREPARATION METHOD FOR ELECTRON HOLOGRAPHY

(75) Inventors: Thomas A. Bauer, Poughkeepsie, NY (US); Steven H. Boettcher, Fishkill, NY (US); Anthony G. Domenicucci, New Paltz, NY (US); John G. Gaudiello, Poughkeepsie, NY (US); Leon J. Kimball, Montgomery, NY (US); Jeffrey S. McMurray, Wappingers Falls, NY (US); Yun-Yu Wang, Poughquag, NY (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 10/711,690

(22) Filed: Sep. 30, 2004

(65) Prior Publication Data
US 2006/0065830 A1    Mar. 30, 2006

(51) Int. Cl.
*G01N 1/32* (2006.01)
*G01N 23/04* (2006.01)

(52) U.S. Cl. ............... 250/307; 250/311; 250/397; 250/452.21; 250/309; 438/14; 438/197; 438/98

(58) Field of Classification Search ............. None
See application file for complete search history.

(56) References Cited

U.S. PATENT DOCUMENTS 6,218,663 B1    4/2001  Nisch et al.
6,759,656 B2 *  7/2004  Tomita ................ 250/311

OTHER PUBLICATIONS

K. Heinz et al.; "Holographic Low-Energy Electron Diffraction;" Journal of Physics: Condensed Matter 13 (2001); pp. 10647-10663.
Electron Holography: A New View of Material Structure, [online]; [retrieved on Jul. 22, 2004]; retrieved from the Internet at www.oml.gov/info/omlreview/rev28-4/text/electron.htm.
M-Bond 610 Adhesive System, [online]; [retrieved on Jul. 26, 2004]; retrieved from the Internet at www.2.spi.com/catalog/spec_prep/glue.shtml.

* cited by examiner

*Primary Examiner*—Nikita Wells
*Assistant Examiner*—Zia R. Hashmi
(74) *Attorney, Agent, or Firm*—Cantor Colburn LLP

(57) ABSTRACT

A method for preparing a transmission electron microscopy (TEM) sample for electron holography includes forming a sacrificial material over an area of interest on the sample, and polishing the sample to a desired thickness, wherein the area of interest is protected from rounding during the polishing. The sacrificial material is removed from the sample following the polishing.

17 Claims, 4 Drawing Sheets

TRANSMISSION ELECTRON MICROSCOPY SAMPLE PREPARATION METHOD FOR ELECTRON HOLOGRAPHY

BACKGROUND OF INVENTION

The present invention relates generally to semiconductor device manufacturing, and, more particularly, to a method for transmission electron microscopy (TEM) sample preparation for electron holography.

Advancements in Transmission Electron Microscopy (TEM) technology enable materials to be analyzed at near atomic resolution by providing high-magnification, high-resolution imaging and analysis capabilities. TEM enables scientists to gather information relating to a material's physical properties, such as its microstructure, crystalline orientation and elemental composition. This information has become increasingly important as the need for advanced materials for use in areas such as microelectronics and optoelectronics, biomedical technology, aerospace, transportation systems and alternative energy sources, among others, increases.

TEM is accomplished by examining material specimens under a transmission electron microscope. In a transmission electron microscope, a series of electromagnetic lenses direct and focus an accelerated beam of electrons, emitted from an electron gun contained within the microscope, at the surface of a specimen. Electrons transmitted through the specimen yield an image of the specimen's structure, which provides information regarding its properties. In addition, elemental and chemical information is provided by both the transmitted electrons and the x-rays that are emitted from the specimen's surface as a result of electron interaction with the specimen.

In 1947, a Hungarian-British physicist named Dennis Gabor sought to find a way to sharpen the resolution of the images initially produced in transmission electron microscopes, which were in their infancy at the time. He proposed electron holography, a method of interference imaging in which the phase and amplitude components of the electron beam are separated to correct the spherical aberration of the microscope. In this regard, the electron beam source is split into the incident, undeviated electron wave (i.e., the reference wave) and the image wave (or object wave) diffracted by the specimen and exiting the bottom surface thereof. Assuming the electron optical geometry is correctly set up, these two waves can be made to interfere. The resulting interference pattern is then processed using optical techniques to form the holograms (images).

Unfortunately, the electron microscopes of Gabor's era did not produce an electron wave with sufficient coherence to permit the proper degree of interference required to make a useful hologram. More recently however, the development of TEMs using highly coherent field-emission electron sources has made electron holography a more effective undertaking. This technique has been shown to be particularly valuable for two-dimensional, p-n junction potential mapping of semiconductor devices with high spatial resolution. Such information is valuable for semiconductor device development and yield improvement.

Before a specimen can be analyzed using TEM (including electron holography), it must be prepared using various techniques to achieve the necessary electron transparency as it is necessary for the electron beam to transmit through the specimen. This electron transparency is accomplished by thinning a defined area of the specimen. For equal resolution, the required thickness of the specimen is dependent on the accelerating voltage of the transmission electron microscope. For example, using a 120 kV microscope, the specimen thickness should be on the order of about 100 to about 2000 angstroms (Å). In contrast, A 1,000 kV microscope can tolerate a specimen thickness of up to about 5,000 Å.

Specimens are prepared through several well-known methods, including, but not limited to, electrolytic thinning, mechanical polishing, ultramicrotomy, crushing, and ion milling. Often times, multiple methods are utilized to prepare a single specimen. Normal TEM sample preparation utilizes a deposited material such as tetraethyl orthosilicate (TEOS) on top of the sample in order to protect it from cracking and rounding during a subsequent polishing operation. If the sample becomes rounded, then subsequent ion milling may cause re-deposition of material on the shadow region near the top surface. This in turn results in a rough surface formed on the sample and leads to a noisy phase map for electron holography.

However, for electron holography, any protective material formed over the sample would need to be removed prior to the imaging, due to the requirement of having a vacuum region near the area of interest for a reference electron wave to pass. A conventionally deposited material such as TEOS cannot be removed (i.e., etched away) without attacking the sample itself. Accordingly, it would be desirable to be able to provide a protective layer during electron holography sample preparation in a manner that also allows for the removal of the protective layer prior to imaging.

SUMMARY OF INVENTION

The foregoing discussed drawbacks and deficiencies of the prior art are overcome or alleviated by a method for preparing a transmission electron microscopy (TEM) sample for electron holography. In an exemplary embodiment, the method includes forming a sacrificial material over an area of interest on the sample, and polishing the sample to a desired thickness, wherein the area of interest is protected from rounding during the polishing. The sacrificial material is removed from the sample following the polishing.

In another embodiment, a method for preparing a transmission electron microscopy (TEM) sample for electron holography includes forming a sacrificial material over an area of interest on the sample, and forming a protective layer over the sacrificial material. The sample is polished to a desired thickness, wherein the area of interest is protected from rounding during the polishing, and the sacrificial material and the protective layer are removed from the sample following the polishing.

BRIEF DESCRIPTION OF DRAWINGS

Referring to the exemplary drawings wherein like elements are numbered alike in the several Figures.

DETAILED DESCRIPTION

Disclosed herein is a method for preparing a transmission electron microscopy (TEM) sample specifically for electron holography, in which the sample is protected cracking and rounding during polishing thereof. Briefly stated, a sacrificial protective layer is formed over the sample such that once the polishing operation is complete, the protective layer may be removed in a manner that does not attack the topography of the sample. In another embodiment, the protective layer is formed over the sacrificial layer such that once the sacrificial layer is removed, the protective layer is also removed from the sample.

Figure 1:
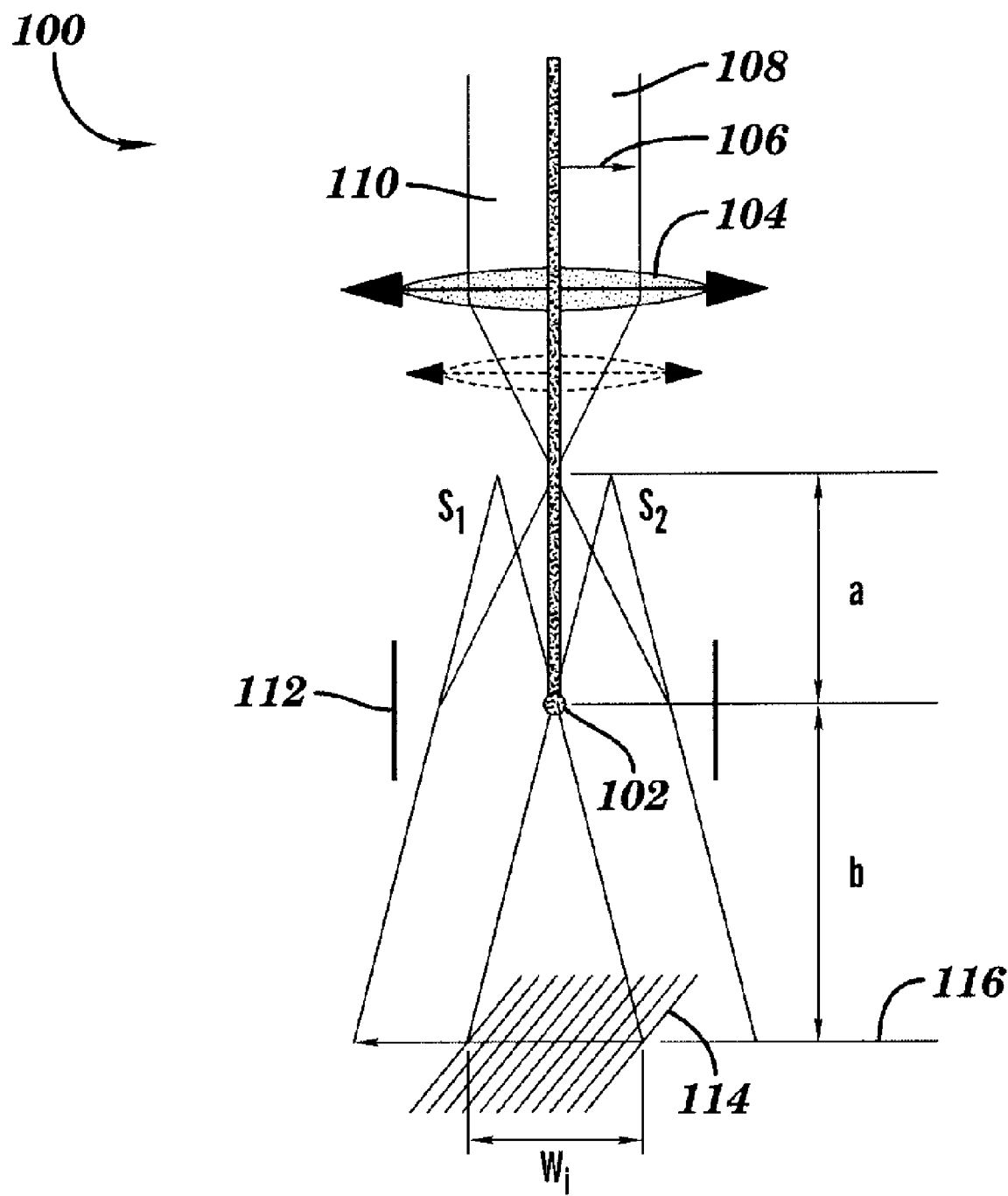
FIG. 1 is a schematic diagram of an electron holography imaging system.

Referring initially to FIG. 1, there is shown a schematic diagram of an electron holography imaging system 100. Employing an electronic bi-prism, the system 100 includes an ultrafine (e.g., about 0.5 micron diameter) fiber 102 positioned in an imaging lens 104 perpendicular to the electron beam such that it splits the resulting field of view. A thin TEM specimen 106 is placed over one side of the image field of the electron beam source such that an object beam 108 passes through the specimen 106, while the other side of the image field is the reference beam 110.

When a positive voltage is applied to the fiber 102 through a voltage source 112, the electron waves on either side of the fiber are bent toward the center, and event ally causing them to overlap. This simulates a pair of holographic image sources S1, S2 at a distance, a, from the end of the positively charged fiber 102. The overlapping waves interfere with one another, creating an interference pattern of parallel fringes 114 at an image plane 116, which is a distance, b, from the end of fiber 102. Depending upon how the specimen 106 affects the electron beam, the fringes will change in position and in contrast to one another. As indicated previously, the area of interest on a sample should be as close to the vacuum of the reference beam as possible such that the reference beam passes through the entire sample. Thus, it is not practical to maintain a protective coating on top of the area of interest for electron holography.

Figure 2:
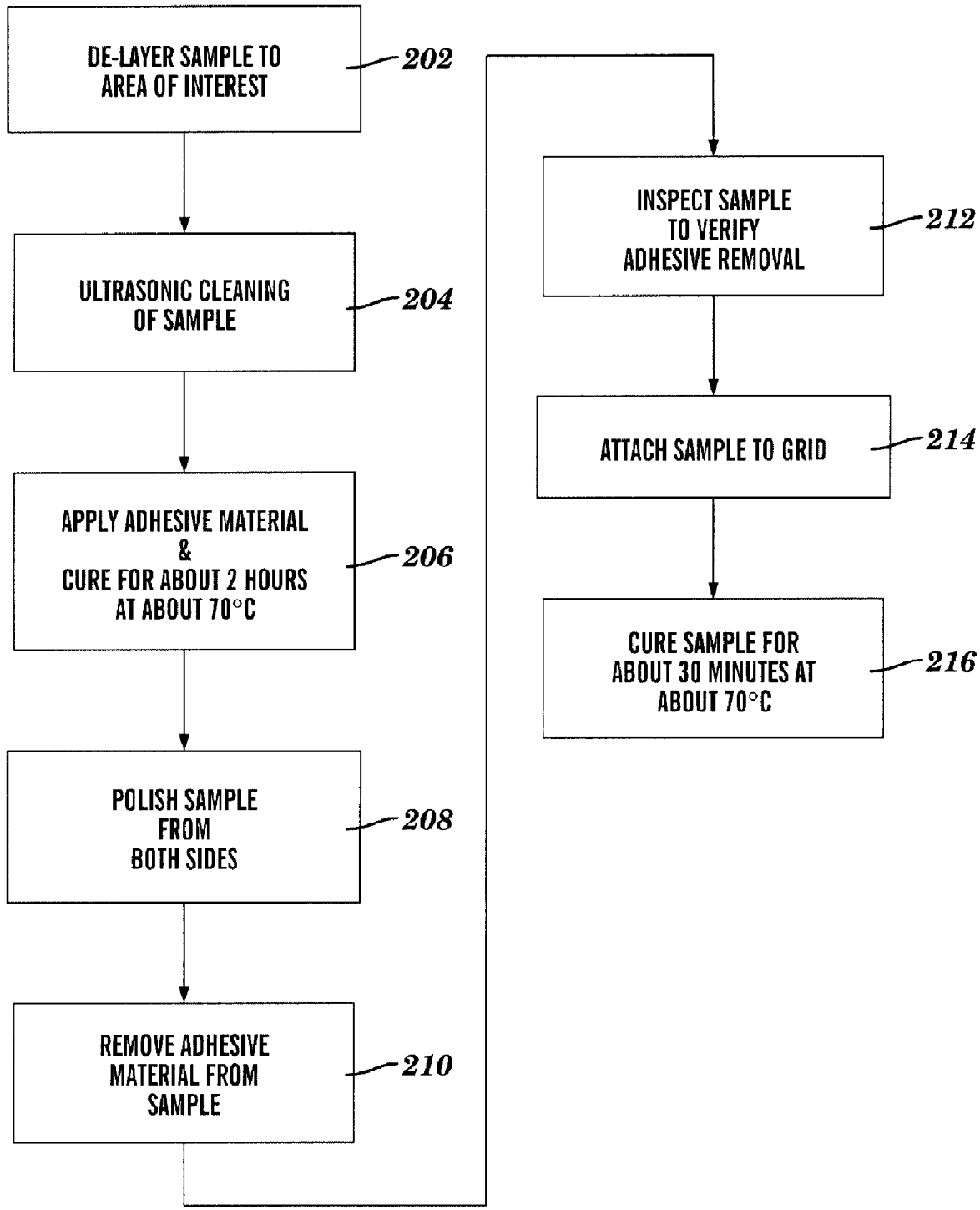
FIG. 2 is a process flow diagram illustrating a method for preparing a TEM sample for electron holography, in accordance with an embodiment of the invention.

Therefore, in accordance with an embodiment of the invention, FIG. 2 is a process flow diagram illustrating a method 200 for preparing a TEM sample for electron holography. As shown in block 202, a TEM sample is de-layered down to the area of interest, such as to the top of a polysilicon gate contact, for example. The amount of de-layering depends on the desired field of view and the spatial resolution. This may be implemented, for example, through finger polishing with 0.3 micro $AlO_3$ on a black pad. Optionally, the de-layering down to the polygate contact could be verified by scanning electron microscope (SEM) at this point. Then, at block 204, the sample is ultrasonically cleaned in an acetone (or alcohol) solution for about 10 minutes in order to clear the surface of the sample so as to avoid subsequent delamination of a sacrificial protective material applied thereon.

Proceeding to block 206, a sacrificial adhesive material is applied over the sample and oven-cured for about two hours at a temperature of about 70° C. A suitable adhesive material, for example, is M-Bond™, an organic, epoxy-phenolic resin. The resin material may be coated onto the sample by brush application. Once the adhesive material is cured, the sample may then be polished from both sides in order to achieve the desired thickness of the sample, as shown in block 208. Observation of the color fringe of the sample may be used as a means of polishing endpoint detection. Another acetone cleaning step may then be implemented to release the sample from the polishing apparatus.

For electron holography applications, the protective adhesive material is removed prior to imaging of the sample. Thus, at block 210, a reagent such as ammonium hydroxide ($NH_4OH$), for example, is used to strip the adhesive resin but without attacking the semiconductor (silicon) material of the sample. In an exemplary embodiment, the sample is immersed in a 30% $NH_4OH$ solution for at least one hour to remove the adhesive. An optical microscope may thereafter be used to visually inspect the sample to verify the adhesive is in fact removed, as shown at block 212. The prepared sample is mounted to a grid (such as through M-Bond™ adhesive) at block 214, and is readied for electron holography imaging after another curing step for about 30 minutes at a temperature of about 70° C. as shown in block 216.

Figure 3:
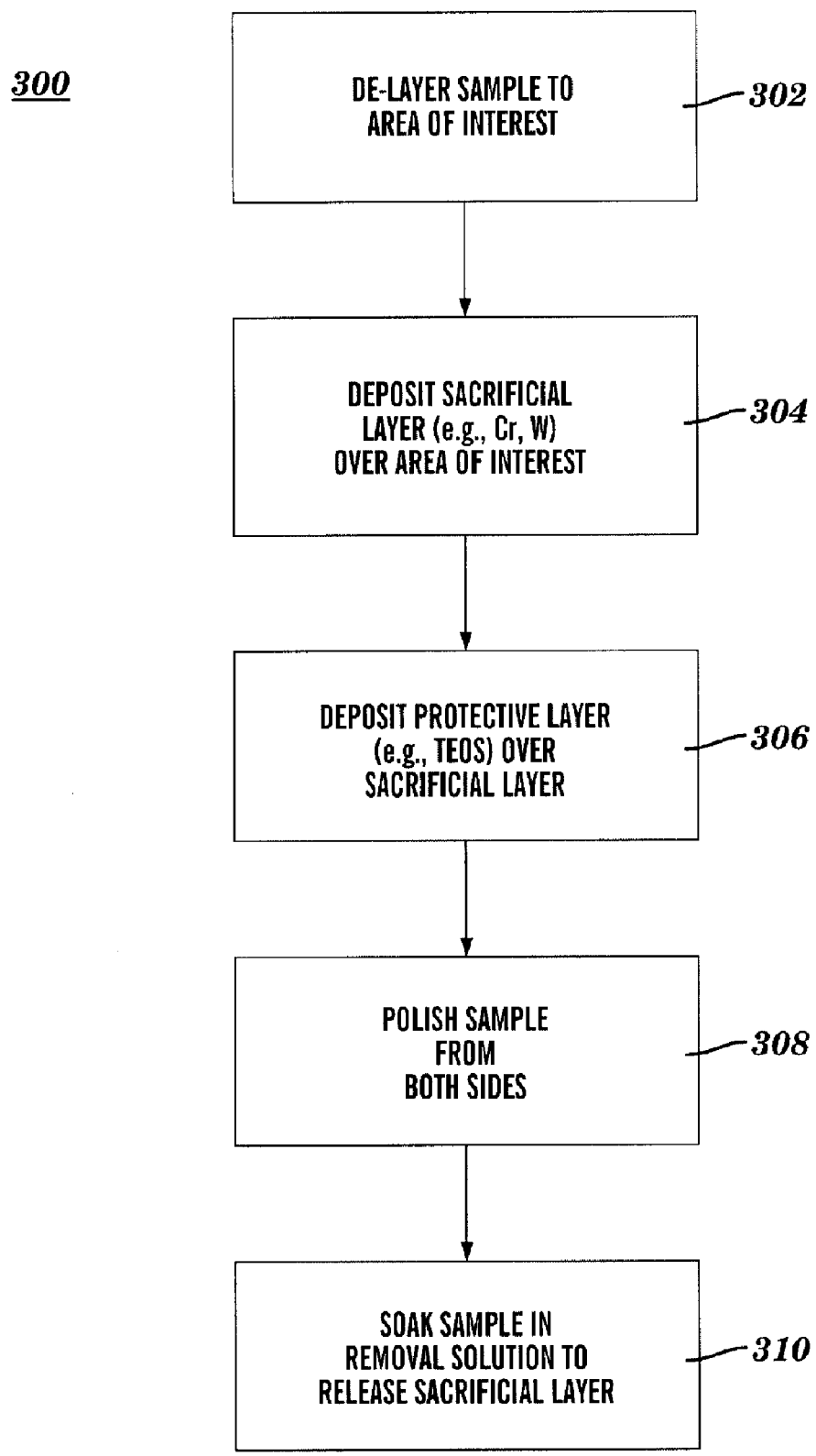
FIG. 3 is a process flow diagram illustrating a method for preparing a TEM sample for electron holography, in accordance with an alternative embodiment of the invention.

FIG. 3 is a process flow diagram illustrating a method 300 for preparing a TEM sample for electron holography, in accordance with an alternative embodiment of the invention. As shown in block 302, the TEM sample is de-layered down to the area of interest, similar to the embodiment of FIG. 2. In lieu of an adhesive material, a sacrificial layer such as chromium (Cr) or tungsten (W) is deposited over the area of interest, as shown in block 304. Then, a protective layer such as TEOS is formed atop the Cr (or W) sacrificial layer, as shown in block 306.

At this point, (after an optional cleaning step) the sample is polished from both sides until the desired sample thickness is achieved, as indicated in block 308. Again, suitable polishing endpoint detection and other inspection techniques may be implemented to verify desired sample thickness. Then, as shown in block 310, the sample is immersed in a Cr (or W) removal solution so as to release the sacrificial Cr (or W) layer and, consequently, the protective TEOS layer thereon. As with the embodiment of FIG. 2, the sample has been protected from chipping and rounding during polishing, and the protective/sacrificial layers are then capable of being removed without damaging the sample itself.

Figure 4:
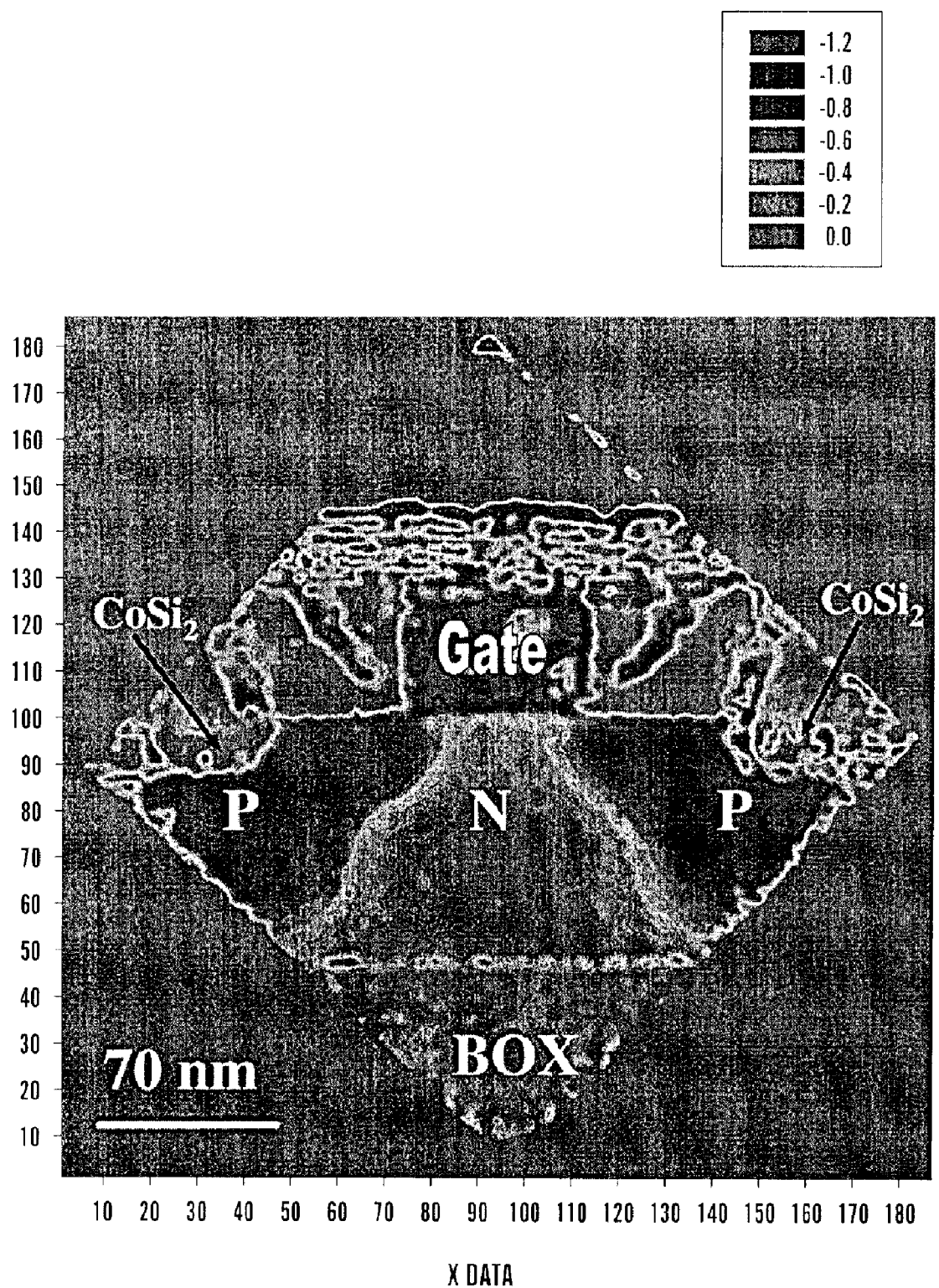
FIG. 4 is an exemplary electron holography image of a semiconductor device generated using the adhesive release embodiment of FIG. 2.

Finally, FIG. 4 is an exemplary electron holography image 400 of a semiconductor device generated using the adhesive release embodiment of FIG. 2. As is shown, the exemplary image 400 depicts the silicidation of the diffusion regions ("P") and the gate contact ("Gate") of a silicon-on-insulator (SOI) device with $CoSi_2$. By protecting this sample area during polishing and removing the material used to protect the layer, a quality inspection image is obtained.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for preparing a transmission electron microscopy (TEM) sample for electron holography, the method comprising:

forming a sacrificial material over an area of interest on the sample;

polishing the sample to a desired thickness, wherein said area of interest is protected from rounding during said polishing; and removing said sacrificial material from the sample following said polishing.

2. The method of claim 1, wherein said sacrificial material comprises an adhesive material.

3. The method of claim 2, wherein said adhesive material comprises an organic, epoxy-phenolic resin.

4. The method of claim 3, further comprising oven curing said adhesive material following the formation thereof on the sample.

5. The method of claim 4, wherein said adhesive material is cured for about for about two hours at a temperature of about 70° C.

6. The method of claim 2, wherein said adhesive material is removed by an ammonium hydroxide ($NH_4OH$) solution so as to leave said area of interest substantially intact.

7. The method of claim 1, further comprising de-layering the sample down to the area of interest prior to said forming said sacrificial material.

8. The method of claim 7, further comprising ultrasonically cleaning the sample prior to said forming said sacrificial material.

9. The method of claim 8, further comprising applying an acetone solution to said sample following said polishing.

10. The method of claim 6, further comprising optically inspecting the sample following the removal of said adhesive material.

11. A method for preparing a transmission electron microscopy (TEM) sample for electron holography, the method comprising:

forming a sacrificial material over an area of interest on the sample;

forming a protective layer over said sacrificial material;

polishing the sample to a desired thickness, wherein said area of interest is protected from rounding during said polishing; and removing said sacrificial material and said protective layer from the sample following said polishing.

12. The method of claim 11, wherein said sacrificial material comprises at least one of a chromium (Cr) and a tungsten (W) layer.

13. The method of claim 12, wherein said protective layer comprises a tetraethyl orthosilicate (TEOS) layer.

14. The method of claim 12, wherein said sacrificial material is removed by soaking the sample in a removal solution so as to leave said area of interest substantially intact.

15. The method of claim 11, further comprising de-layering the sample down to the area of interest prior to said forming said sacrificial material.

16. The method of claim 15, further comprising ultrasonically cleaning the sample prior to said forming said sacrificial material.

17. The method of claim 14, further comprising optically inspecting the sample following the removal of said adhesive material.

* * * * *